(12) United States Patent
Fournier

(10) Patent No.: US 9,849,164 B2
(45) Date of Patent: Dec. 26, 2017

(54) ENZYME FORMULATION FOR REDUCING HISTAMINE INTOLERANCE

(71) Applicant: Thea Fournier, North Andover, MA (US)

(72) Inventor: Thea Fournier, North Andover, MA (US)

( * ) Notice: Subject to any disclaimer, the term of this patent is extended or adjusted under 35 U.S.C. 154(b) by 0 days.

(21) Appl. No.: 15/079,404

(22) Filed: Mar. 24, 2016

(65) Prior Publication Data

US 2017/0274056 A1    Sep. 28, 2017

(51) Int. Cl.
*A61K 38/43* (2006.01)
*A61K 38/54* (2006.01)
*A61K 9/48* (2006.01)

(52) U.S. Cl.
CPC ............ *A61K 38/54* (2013.01); *A61K 9/4816* (2013.01); *C12Y 302/01* (2013.01); *C12Y 302/01001* (2013.01); *C12Y 302/01022* (2013.01); *C12Y 302/01108* (2013.01); *C12Y 303/01* (2013.01); *C12Y 304/14005* (2013.01); *C12Y 402/02002* (2013.01)

(58) Field of Classification Search
None
See application file for complete search history.

(56) References Cited

PUBLICATIONS

Wolfson et al., "Making Sense of Digestive enzymes", KLAIRE Labs, Technical Summary, 2008, p. 1-8.*
Maintz and Novak, Am J Clin Nutr, 2007, vol. 85, p. 1185-1196.*
Ku et al. CAPSUGEL, Performance Qualification of a New Hypromellose Capsule, 2011, p. 1-15 +1.*

* cited by examiner

*Primary Examiner* — Kade Ariani
(74) *Attorney, Agent, or Firm* — Eric P. Mirabel

(57) ABSTRACT

Disclosed is a formulation of the following enzymes: Alpha-galactosidase, Alpha amylase, Beta Glucanase, Lactase, BioCor DPP=IV (Proprietary blend) and Pectinase, which has been found to be effective in treating histamine intolerant people, and causing a significant improvement in a wide variety of pathologies and symptoms, including, but not limited to: inflammation, pruritus, urticaria, hypotension, tachycardia, fatigue, migraines, conjunctivitis, incontinence, nasal congestion, panic attacks, acid reflux, depression and angioedema.

6 Claims, No Drawings

ENZYME FORMULATION FOR REDUCING HISTAMINE INTOLERANCE

BACKGROUND

In the past six years or so, there has been an increase in research about histamine intolerance, which has generated clinical evidence of it, and more internet sites with options to help those who are intolerant. It is believed that many who are intolerant to histamine can have the intolerance traced to genetically engineered foods ("GMO foods") that have created a disturbance of the "gut biome," or intestinal bacteria, damaging gut health. In susceptible individuals, these changes in the gut biome create a condition called "histamine intolerance." This has also contributed to deficiencies in the body's histamine breakdown process, which involve the DAO enzyme and the N-methyltransferase (HMT) enzyme. These susceptible individuals, who cannot efficiently break down histamine, react to the excessive accumulation of histamine in their bodies.

There are many sources that increase histamine in the body which include, but are not limited to: (1) Foods that naturally contain this chemical compound, including, but not limited to: fermented foods, yogurt, kefir, citrus fruits, most berries, dried fruits, tomatoes, spinach, chocolate, vinegar, and eggs; (2) Some foods, like nuts and seeds, though containing no histamine, can trigger a release of histamine in the body; (3) Leftovers (The longer food is stored, the greater its histamine content); (4) An over-growth of certain bacteria in the GI tract, which can produce an excess of histamine; (5) Certain strains of probiotics, and (6) Stress.

Over the past ten years, the inventor found that by reducing histamine intake in the body through daily appropriate dietary choices, though challenging and often problematic, appears to be highly effective in treating a wide range of histamine-related symptoms and conditions, including, but not limited to: inflammation, pruritus, urticaria, hypotension, tachycardia, fatigue, migraines, conjunctivitis, incontinence, nasal congestion, panic attacks, acid reflux, depression and angioedema. The invention herein relates to a novel formulation for treatment and prevention of histamine-related conditions.

SUMMARY

A formulation of the following enzymes: Alpha-galactosidase, Alpha amylase, Beta Glucanase, Lactase, BioCor DPP-IV (National Enzyme Company, Inc., Forsyth, Mo.), and Pectinase (the "Formulation"), has been found to be effective in treating histamine intolerant people, or preventing symptoms, and causing a significant improvement in a wide variety of symptoms/conditions, including, but not limited to: inflammation, pruritus, urticaria, hypotension, tachycardia, fatigue, migraines, conjunctivitis, incontinence, nasal congestion, panic attacks, acid reflux, depression and angioedema. It is believed that the Formulation helps to rebalance the "gut biome" and to restore deficiencies that support the body's overall histamine breakdown process, thereby reducing the accumulation of histamine in the body.

More particularly, the preferred dosages of the enzymes in the Formulation are as follows: Alpha-galactosidase: 80 GaLU; Alpha amylase: 150 DU; Beta Glucanase: 70 BGU; Lactase: 1,000 ALU; BioCor DPP-IV Proprietary blend, 80 mg, and Pectinase: 17 ENDO-PGU. The preferred dosing is ingesting two or more capsules of the Formulation with the foregoing contents with each meal. A preferred carrier for the Formulation is a vegetable capsule (including, mostly cellulose and distilled water). The Formulation should be free of any of the following: milk/casein, gluten, dairy, egg, soy, corn, peanuts, tree nuts, fish and shellfish, and should not contain any artificial colors, flavors or preservatives.

A discussion of testing and demonstrating the safety and efficacy of the formulation is set forth below in the Detailed Description.

DETAILED DESCRIPTIONS

The treatment and prevention regime with the formulation of the invention will now be described in greater detail with reference to the example below of an administration regime and testing with a number of patients.

Example: Administering the Formulation to Screened Patients

A questionnaire shall be administered to twenty or more patients who are chronically reactive to the excessive accumulation of histamine in the body. These are patients who present a variety of symptoms, including, but not limited to one or more of: pruritus, urticaria, hypotension, tachycardia, fatigue, conjunctivitis, incontinence, nasal congestion, panic attacks, acid reflux, depression and angioedema. All the patients will have been mindfully eating a low histamine diet for three or more months, minimizing histamine producing bacteria and maximizing histamine degrading bacteria. They will have made dramatic improvements while managing their diets, but continue to have episodic symptoms because histamine intolerance is cumulative, i.e., it is not always immediate and is difficult to mitigate.

The formulation will then be administered to each patient. Over a three month period, patients symptoms will be monitored at monthly visits. After three months on the formulation, a follow-up questionnaire will be administered to determine if their episodic symptoms have improved and if their histamine intolerance has been reduced.

The preferred dosages and dosing regime for the formulation, as set forth in the Summary, are not the only dosages possible, and other more optimal dosages and dosing regimes may be discovered with routine experimentation, now that the preferred dosages are known. The routine experimentation would involve providing different dosages under different regimes, using behavioral kinesiology to determine the appropriate dosage and optimal regime for each individual child or adult in the case study, and determining which patients improved most in their monitored symptoms and conditions.

The starting point, for determining optimal dosing and an optimal regime, is the preferred dosages, administered at mealtimes, as above. Variations could be doubling, halving, or otherwise and reducing the quantities of one or more of the enzymes in a formulation. The dosing regime modifications could include increasing or reducing the number of administrations of the formulation each day for patients in a particular group. Such experimentation is routine in the pharmaceutical industry.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method for treating one or more histamine-related symptoms selected from pruritus, fatigue, nasal congestion, panic attacks and angioedema in a subject in need, the method comprising administering to the subject in need a formulation including: Alpha-galactosidase, Alpha amylase, Beta Glucanase, Lactase, DPP-IV and Pectinase thereby treating said one or more histamine-related symptoms.

2. The method of claim 1 wherein the ingredients are in the formulation at the following quantities: Alpha-galactosidase: 80 GaLU; Alpha amylase, 150 DU; Beta Glucanase, 70 BGU; Lactase, 1,000 ALU; DPP-IV, 80 mg, and Pectinase: 17 ENDO-PGU.

3. The method of claim 1 wherein the ingredients are administered to the subject at twice the quantities therein with each meal consumed.

4. The method of claim 1 wherein the formulation is encapsulated in a capsule.

5. The method of claim 1 wherein the formulation does not contain any of the following milk, casein gluten, dairy, egg, soy, corn, peanuts, tree nuts, fish, shellfish, and, artificial colors, flavors or preservatives.

6. The method of claim 1 wherein the formulation is administered at least once per day.

* * * * *